US009539182B2

(12) United States Patent
Morris et al.

(10) Patent No.: US 9,539,182 B2
(45) Date of Patent: Jan. 10, 2017

(54) COATED DENTAL ARTICLES AND RELATED METHODS OF MANUFACTURE

(76) Inventors: Geoffrey P. Morris, White Bear Lake, MN (US); William E. Wyllie, II, Pasadena, CA (US); Steven D. Theiss, Woodbury, MN (US)

( * ) Notice: Subject to any disclaimer, the term of this patent is extended or adjusted under 35 U.S.C. 154(b) by 77 days.

(21) Appl. No.: 13/812,006

(22) PCT Filed: Aug. 22, 2011

(86) PCT No.: PCT/US2011/048545
§ 371 (c)(1),
(2), (4) Date: Jan. 24, 2013

(87) PCT Pub. No.: WO2012/030565
PCT Pub. Date: Mar. 8, 2012

(65) Prior Publication Data
US 2013/0157225 A1  Jun. 20, 2013

Related U.S. Application Data

(60) Provisional application No. 61/378,002, filed on Aug. 30, 2010.

(51) Int. Cl.
*A61C 7/00* (2006.01)
*A61K 6/06* (2006.01)
(Continued)

(52) U.S. Cl.
CPC ............... *A61K 6/0681* (2013.01); *A61C 5/10* (2013.01); *A61C 7/00* (2013.01); *A61C 7/14* (2013.01);
(Continued)

(58) Field of Classification Search
CPC ............ A61C 7/00; A61C 7/14; A61C 13/00; A61C 13/09; A61C 5/10; A61C 7/28; A61C 8/00
(Continued)

(56) References Cited

U.S. PATENT DOCUMENTS 3,964,165 A  6/1976  Stahl
4,299,569 A  11/1981  Frantz
(Continued)

FOREIGN PATENT DOCUMENTS

EP  1820786  8/2007
EP  2263991  12/2010
(Continued)

OTHER PUBLICATIONS

Teixeira et al., "Effect of YSZ Thin Film Coating Thickness on the Strength of a Ceramic Substrate" Journal of Biomedical Materials Research Part B: Applied Biomaterials, vol. 83B, No. 2, Nov. 1, 2007; pp. 459-463.
(Continued)

*Primary Examiner* — Ralph Lewis (57) ABSTRACT

Provided are dental articles, and methods of making articles, having an aesthetic inorganic coating based on zirconia at least partially stabilized with yttrium oxide, calcium oxide, cerium oxide, or magnesium oxide. Stabilized zirconia coatings were found to provide a smooth, low friction surface having high abrasion resistance. These coatings are particularly applicable to orthodontic appliances. While virgin stabilized zirconia coatings can often have an undesirable color cast, it was discovered that this color cast can be substantially eliminated by heat treating the coated appliance in an oxygenated environment. The combination of depositing a stabilized zirconia coating and subsequently heat treating to decolorize the coating provides a surprisingly robust, stable, low-friction coating that is also aesthetic.

20 Claims, 2 Drawing Sheets

(51) Int. Cl.
*A61K 6/00* (2006.01)
*C04B 41/00* (2006.01)
*C04B 41/50* (2006.01)
*C04B 41/87* (2006.01)
*A61C 7/14* (2006.01)
*A61C 7/20* (2006.01)
*A61C 8/00* (2006.01)
*A61C 13/00* (2006.01)
*A61C 5/10* (2006.01)
*A61C 7/28* (2006.01)
*A61C 13/09* (2006.01)
*A61K 6/04* (2006.01)
*C04B 111/00* (2006.01)

(52) U.S. Cl.
CPC .............. *A61C 7/20* (2013.01); *A61C 7/282* (2013.01); *A61C 8/0013* (2013.01); *A61C 13/0006* (2013.01); *A61C 13/09* (2013.01); *A61K 6/0023* (2013.01); *A61K 6/043* (2013.01); *A61K 6/0675* (2013.01); *C04B 41/009* (2013.01); *C04B 41/5042* (2013.01); *C04B 41/87* (2013.01); *C04B 2111/00836* (2013.01)

(58) Field of Classification Search
USPC ................. 433/8–15, 199.1, 212.1, 22.1, 201.1, 433/228.1
See application file for complete search history.

(56) References Cited

U.S. PATENT DOCUMENTS

| | | |
|---|---|---|
| 4,302,532 A | 11/1981 | Wallshein |
| 4,915,625 A | 4/1990 | Tsukuma |
| 4,954,080 A | 9/1990 | Kelly |
| 5,358,402 A | 10/1994 | Reed |
| 5,380,196 A | 1/1995 | Kelly |
| 6,305,932 B1 | 10/2001 | Mottate |
| 6,648,638 B2 | 11/2003 | Castro |
| 6,878,456 B2 | 4/2005 | Castro |
| 6,974,625 B2 * | 12/2005 | Hunter ............ A61F 2/28 428/304.4 |
| 7,655,586 B1 | 2/2010 | Brodkin |
| 2007/0134610 A1 | 6/2007 | Wyllie, II |
| 2010/0086896 A1 * | 4/2010 | Gieselmann ......... A61C 8/0012 433/173 |

FOREIGN PATENT DOCUMENTS

| | | |
|---|---|---|
| KR | 2009-0109204 | 10/2009 |
| WO | 2005/094715 | 10/2005 |

OTHER PUBLICATIONS

International Search Report PCT/US2011/048545 Nov. 17, 2011, 5 pgs.

* cited by examiner

COATED DENTAL ARTICLES AND RELATED METHODS OF MANUFACTURE

FIELD OF THE INVENTION

Provided are dental articles and related methods of manufacture. In more detail, provided are dental articles with inorganic coatings applied thereon and related methods of manufacture.

DESCRIPTION OF THE RELATED ART

Orthodontics is a field of dentistry concerned with the diagnosis and correction of the improper positioning of teeth, or malocclusions. Correction of these malocclusions is desirable for improving bite function, facilitating dental hygiene, and also improving facial appearance.

One particular type of orthodontic therapy, called fixed appliance treatment, involves bonding tiny slotted appliances called brackets to the surfaces of a patient's teeth. A resilient "U"-shaped appliance called an archwire is then secured into the slots of the brackets to initiate treatment. The end portions of the archwire are typically received in the passages of tiny appliances called molar tubes, which are bonded to the patient's molar teeth. The archwire assumes a distorted shape when initially received in the bracket slots, but applies gentle, therapeutic forces to the brackets as it gradually returns to its original, relaxed state. In this manner, the initially maloccluded teeth are guided into their proper positions over the course of treatment. The combination of brackets, molar tubes, and archwire is commonly referred to as "braces."

The efficiency of teeth movement during orthodontic treatment is affected by friction between the archwire and the bonded appliances. The friction between these appliances is, in turn, related to the materials used for those appliances. For example, orthodontic brackets are commonly made from stainless steel, while archwires are commonly made from metals such as stainless steel, beta titanium, or shape memory alloys such as nickel-titanium. In general, the resistance to sliding between stainless steel brackets and metal archwires, while not insignificant, has been satisfactory to most orthodontists.

However, orthodontic brackets are now available in a variety of materials, including plastic materials (e.g., polycarbonate) and ceramic materials. Ceramic materials, such as monocrystalline and polycrystalline alumina, are particularly popular because they offer high strength, stain-resistance, and provide brackets that are transparent or translucent. By virtue of being transparent or translucent, ceramic brackets allow the natural color of the underlying tooth to be seen, thereby providing improved aesthetics over traditional metal brackets.

Greater frictional forces are often observed to result when brackets and archwires made from different materials are paired with each other. These effects can be related to the chemistry of the materials, differences in modulus, differences in hardness, or combinations thereof. For example, ceramic materials can exhibit a galling effect with archwires, where the hard ceramic materials of the bracket grind notches or other surface defects into the relatively soft materials of the archwire during use. The notches act as barriers that inhibit the free sliding of the archwire along the bracket slot. Galling of the archwire may slow the movement of the teeth, which may accordingly lengthen treatment time.

To address these issues, manufacturers have placed archwire slot liners within the respective bracket slots. Archwire slot liners can improve the strength of the bracket, alleviate galling in instances where the bracket is made of a ceramic material, and reduce the resistance to sliding. Examples of archwire slot liners for plastic brackets are described in U.S. Pat. Nos. 3,964,165 (Stahl), 4,299,569 (Frantz) and 4,302,532 (Wallshein), and examples of archwire liners for ceramic brackets are described in U.S. Pat. Nos. 5,358,402 (Kelly, et al.), 5,380,196 (Kelly, et al.), and 6,305,932 (Mottate). As an alternative to liners, coatings for brackets have also been explored. Various coated bracket concepts are described in published PCT Application WO2005/0947715 (Steen et al.) and US 2007/0134610 (Wyllie et al.).

Friction and abrasion resistance also have relevance in other areas of dentistry. Dental restorations, for example, provide the function and integrity of missing tooth structure and ideally have surface properties that match those of natural teeth. Tooth enamel is the hardest substance found in the human body and it can be technically challenging to engineer a dental material to have an abrasion resistance such that the restorative wears at the same rate as the restored tooth. This could be particularly relevant when dealing with patients prone to bruxism, or grinding of the teeth. Ideally, dental restoratives have frictional properties that are similar to those of enamel.

Common restorations include inlays and onlays, crowns, bridges, and veneers. Traditional restoration materials are made from metal, such as gold or silver amalgam, and are shaped and bonded to the tooth permanently using dental cements. While these materials provide good friction and abrasion resistance, they are generally not aesthetic. Composite fillings and restorations are translucent and can be selected to match the color of the tooth, allowing for improved aesthetics. However, these materials have a significantly shortened lifespan because their strength and abrasion resistance are lower than that of metal restorations. Composite materials are also more prone to wear and discoloration.

SUMMARY OF THE INVENTION

Described herein are dental articles having an aesthetic inorganic coating based on zirconium oxide (or zirconia) stabilized with an alloying compound such as yttrium oxide (or yttria), calcium oxide, cerium oxide, or magnesium oxide. Stabilized zirconia coatings were found to provide a smooth, low friction surface having high abrasion resistance. These coatings are highly suitable for various dental applications, including orthodontic appliances. For example, a coated orthodontic bracket could facilitate archwire sliding during orthodontic treatment. These inorganic coatings can be applied by physical vapor deposition at low pressures using a radio frequency sputtering unit and, for example, a stabilized zirconia target. While virgin stabilized zirconia coatings can often have an undesirable color cast, it was discovered that this color cast can be substantially eliminated by heat treating the coated appliance in an oxygenated environment. The combination of depositing a stabilized zirconia coating and subsequently heat treating the coating to decolorize the same provides a surprisingly robust, stable, low-friction coating that is also aesthetic.

In one aspect, a method of making a coated dental article is provided. The method comprises providing a dental article having an outer surface, and depositing on at least a portion of the outer surface a coating comprising zirconia that is at least partially stabilized by an alloying compound selected from the group consisting of yttrium oxide, calcium oxide, cerium oxide, magnesium oxide and combinations thereof.

In another aspect, a method of making a coated dental article is provided, comprising providing a dental article having an outer surface, depositing on at least a portion of the outer surface a coating comprising zirconia that is at least partially stabilized by an alloying compound selected from the group consisting of yttrium oxide, calcium oxide, cerium oxide, magnesium oxide and combinations thereof, and heat-treating the coating in an oxygenated environment at a temperature ranging from 300 to 900 degrees Celsius to decolorize the coating.

In still another aspect, a coated dental article is provided, comprising a dental article having an outer surface and a coating extending across at least a portion of the outer surface, the coating comprising a zirconia alloy, the zirconia alloy comprising an alloying compound selected from the group consisting of yttrium oxide, calcium oxide, cerium oxide, magnesium oxide, and combinations thereof.

DEFINITIONS

As used herein:
"Mesial" means in a direction toward the center of the patient's curved dental arch.
"Distal" means in a direction away from the center of the patient's curved dental arch.
"Occlusal" means in a direction toward the outer tips of the patient's teeth.
"Gingival" means in a direction toward the patient's gums or gingiva.
"Facial" means in a direction toward the patient's lips or cheeks.

DETAILED DESCRIPTION OF THE PREFERRED EMBODIMENTS

Stabilized Zirconia Coated Appliances

The above-identified drawing figures set forth several embodiments of the invention. However, other embodiments are also contemplated, as shall be noted herein. The figures may not be drawn to scale. Like reference numbers have been used throughout the figures to denote like parts.

As used herein, dental articles include materials and appliances suitable for use in the oral environment. These include, but are not limited to, orthodontic appliances, restoratives, replacements, inlays, onlays, veneers, full and partial crowns, bridges, implants, implant abutments, copings, anterior fillings, posterior fillings, cavity liners, and bridge frameworks. Orthodontic appliances, as used herein, include brackets, tubes, cleats, buttons and archwires. The present disclosure provides dental articles, and related methods of manufacturing the same, for applications that benefit from improved aesthetics, reduced friction, greater resistance to abrasion, or combinations thereof.

Figure 1:
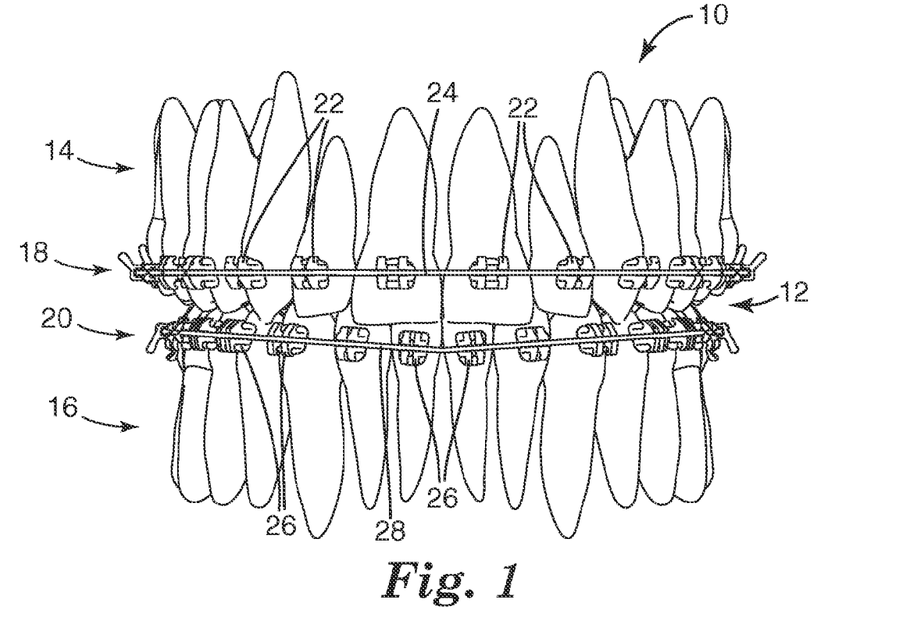
FIG. 1 is a front view of teeth of an exemplary patient undergoing orthodontic treatment with an orthodontic appliance of the present invention.

An exemplary embodiment is shown in FIG. 1. In this figure, teeth undergoing orthodontic treatment are broadly designated by the numeral 10. The teeth 10 include upper dental arch 14 and lower dental arch 16 and are bonded with orthodontic appliances 12. The orthodontic appliances 12 include an upper orthodontic brace 18 and a lower orthodontic brace 20, connected to the upper and lower dental arches 14, 16, respectively. Together, the braces 18, 20 impart corrective forces to the teeth 10 during the course of treatment.

The upper orthodontic brace 18 includes a plurality of brackets 22 and a curved archwire 24. As shown in FIG. 1, each bracket 22 is bonded to a tooth 12 of upper dental arch 14. The archwire 24 extends along the facial surfaces of the upper dental arch 14 and engages with each bracket 22. Similarly, the lower orthodontic brace 20 includes a plurality of brackets 26 and an archwire 28. Each bracket 26 is bonded to a tooth 12 of the lower dental arch 16, and the archwire 28 extends along the facial surfaces of the lower dental arch 16 and engages with each bracket 26.

Figure 2:
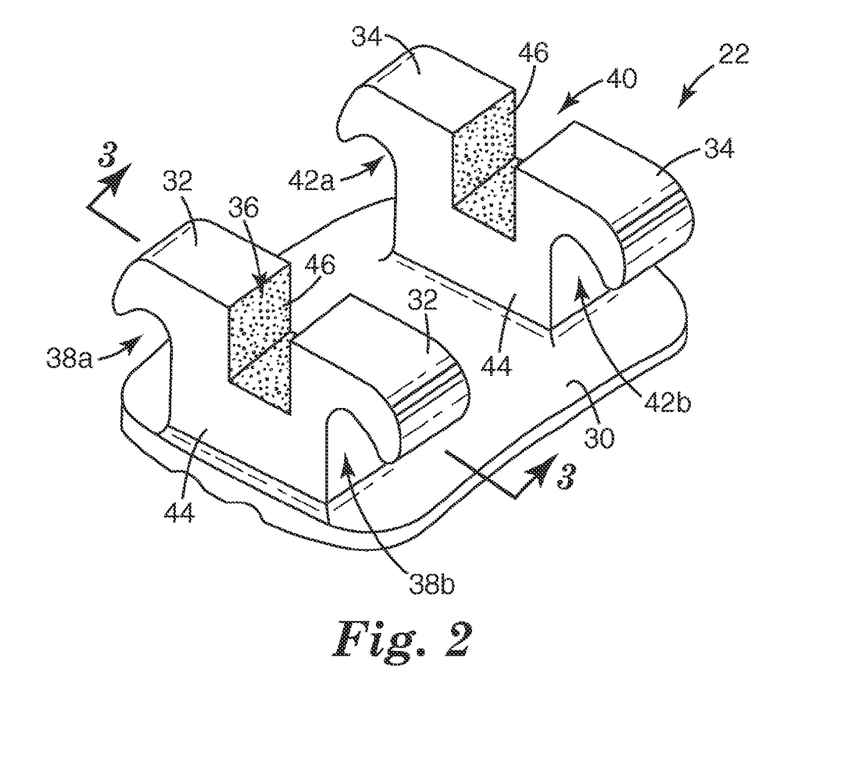
FIG. 2 is a top perspective view of a bracket of the orthodontic appliance of the present invention.

FIG. 2 shows an enlarged view of an individual bracket 22 in the orthodontic brace 18. In this discussion, FIGS. 2-4 refer only to the components of upper orthodontic brace 18 (i.e., brackets 22 and archwire 24). However, it is to be understood that this description applies by analogy to the components of the lower orthodontic brace 20 (i.e. the brackets 26 and the archwire 28). As shown in FIG. 2, the bracket 22 includes a base 30 and mesial and distal bodies 44 extending outwardly from the base 30. The opposite-facing surface of the base 30 is adapted for adhesive coupling to a tooth surface.

An archwire slot 36 commonly extends across bodies 44 in a generally mesial-distal direction to accommodate the archwire 24. Mesial and distal tiewings 32, 34 extend from respective bodies 44 in occlusal and gingival directions. As shown, the tiewings 32,34 present undercuts 38a, 38b, 42a, 42b that allow an elastomeric O-ring or ligature wire (not shown) to be stretched over the archwire 24 on the mesial and distal sides of the bracket 22 and tucked under the tiewings 32, 34 such that the archwire 24 is secured in the archwire slot 36. As denoted by the shaded portions in FIG. 2, a coating 46 extends across surfaces of the archwire slot 36 that potentially contact the archwire 24 during treatment.

Figure 3:
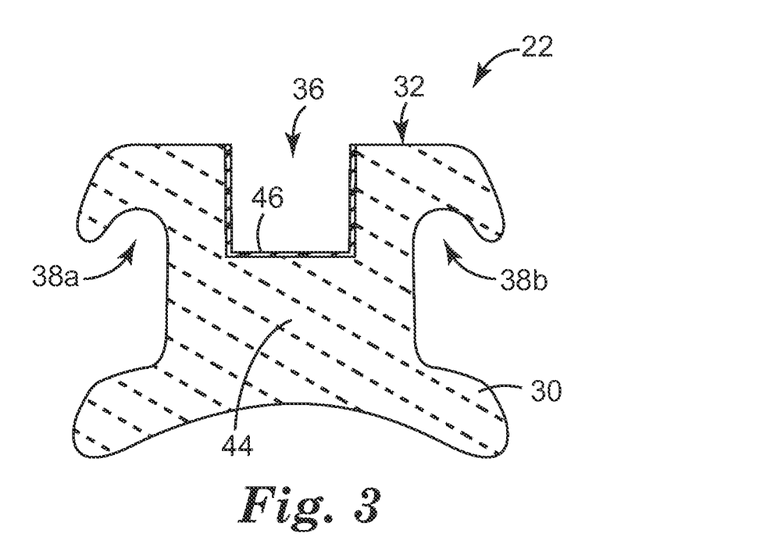
FIG. 3 is a sectional view of section 3-3 taken in FIG. 2, showing cross-sectional components of the bracket.

FIG. 3 presents a sectional view defined by the section 3-3 of the bracket 22 in FIG. 2. As shown, the coating 46 extends across the side walls and bottom wall of the archwire slot 36. If desired, the coating 46 may extend across fewer than all three walls of the archwire slot 36. On the other hand, the coating 46 may also extend across other portions of the outer surface of the mesial body 44 of the bracket 22. In some embodiments, the coating 46 extends across the entire outer surface of the bracket 22.

The body 44 may compositionally include a variety of materials. Examples of suitable materials for the body 44 include metallic materials (e.g., stainless steel), plastic materials (e.g., polycarbonate), and ceramic materials (e.g., monocrystalline and polycrystalline alumina). Examples of particularly suitable materials for the body 44 include ceramic materials that are generally translucent or transparent, such as those disclosed in U.S. Pat. Nos. 4,954,080 (Kelly et al.) and 6,648,638 (Castro, et al.). The body 44 may be formed with standard techniques for manufacturing orthodontic brackets. Alternatively, the body 44 may be a commercially available orthodontic bracket that is subsequently treated to include the coating 46. Examples of suitable commercially available orthodontic brackets include TRANSCEND-brand and CLARITY-brand ceramic brackets, available from 3M Unitek in Monrovia, Calif.

The coating 46 compositionally includes a zirconia ($ZrO_2$) alloy that is at least partially stabilized by an alloying compound selected from the group consisting of yttrium oxide (yttria), calcium oxide, cerium oxide, magnesium oxide, and combinations thereof. At room temperature, zirconia generally assumes a monoclinic phase structure. The addition of the alloying compound renders the cubic phase structure, which is normally stable at high temperatures (above 1150 degrees Celsius), also stable at room temperature (20 to 25 degrees Celsius).

In some embodiments, the zirconia has an alloying compound composition that ranges from 5 to 15 molar percent, and is sufficient to yield a stable zirconia phase structure. Optionally, lower amounts of the alloying compound can be used, resulting in a partially stabilized zirconia phase structure.

Advantageously, stabilized zirconia coatings provide low-friction surfaces that are both hard and chemically inert. The stabilized zirconia coatings can also be applied as a thin film, while still reducing galling and providing a low-friction surface. Examples of suitable layer thicknesses for coating 46 range from 25 to 1000 nanometers, with particularly suitable layer thicknesses ranging from 400 to 700 nanometers. The thin layers for coating 46 are beneficial because the body 44 may be formed without taking the thickness of coating 46 into consideration. This allows the use of commercially available brackets for the body 44 without modifications to account for the thickness of coating 46.

The yttria-stabilized zirconia coating 46 on the archwire slot 36 provides numerous advantages in orthodontic treatment. First, yttria-stabilized zirconia has been reported to have a lower coefficient of friction compared with alumina, in measurements of dynamic coefficient of friction against stainless steel. Under conditions of classical friction, where there is a zero angle between the archwire 24 and the archwire slot 36, the coating 46 provides reduced resistance to relative sliding movement between the archwire 24 and the bracket 22. Second, the coating 46 serves a protective function by reducing microscopic surface damage, or "galling", from abrasion between the archwire 24 and the archwire slot 36 of the bracket 22. By reducing the degree of galling on the archwire surface, low friction levels can be maintained throughout treatment. By reducing friction, both of these effects facilitate teeth movement, especially during the initial leveling and aligning stage of orthodontic treatment.

The coefficient of friction can vary as a function of the thickness of the yttria-stabilized zirconia coating. In some embodiments, the layer thickness of the coating 46 within the archwire slot 36 is uniform. In other embodiments, the layer thickness is non-uniform and provides differing levels of friction depending on the relative orientations of the archwire 24 and the bracket 22. For example, if contact between the archwire 24 and the bracket 22 primarily occurs along the sidewalls of the archwire slot 36, then the coating can be intentionally made thicker along the sidewall surfaces.

Second, the coating 46 provides an exceptionally glossy finish to the bracket 22. A high level of gloss enhances the aesthetics of the appliance. Not only are glossy appliances generally preferred by patients, but they also blend in with surrounding tooth surfaces, which are generally glossy. Gloss measurements on these coated appliances have shown that coated appliances display a gloss which is significantly higher compared with uncoated orthodontic appliances made by ceramic injection molding. In some embodiments, the coating 46 has a 60 degree gloss value exceeding 150 percent that of the uncoated body 44 of the bracket 22. These measurements can be conducted according to the procedure described in the Examples.

Third, the coating 46 is translucent and displays minimal color cast compared to other inorganic coatings, making them ideal coatings for translucent ceramic brackets. Color measurements can be made based on the Commission Internationale de l'Eclairage L*a*b* scoring system. The three coordinates of the L*a*b* scoring system represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

In some embodiments, the coating 46 displays a difference in a* ("Δa*") value greater than 0.5 relative to an uncoated article for a white reflectance standard background before heat-treatment and a Δa* value of 0.5 or less relative to an uncoated article for a white reflectance standard background after heat-treatment. In some embodiments, the coating displays a Δb* value greater than 1.5 relative to an uncoated article for a white reflectance standard background before heat-treatment and a Δb* value of 1.5 or less relative to the uncoated article for a white reflectance standard background after heat-treatment.

Fourth, the stabilized zirconia can be exploited to enable high temperature post-processing of zirconia-coated dental articles. Unlike conventional zirconia, stabilized zirconia can be heated to high temperatures while avoiding the monoclinic-to-cubic phase transformation, along with its associated volume change. Further, the coefficient of thermal expansion of stabilized zirconia is similar to that of alumina, thereby avoiding substantial relative volume change between the two materials. Volume change is generally undesirable because it can result in de-lamination of the coating. This stability at high temperatures is also significant because it enables high temperature post-processing of stabilized zirconia coatings, which in turn can be exploited to realize properties that were not previously accessible. These advantages will be examined in the subsequent section below.

Fifth, these coatings are free of metallic nickel. Accordingly, these coated appliances are particularly suited for patients who have nickel allergies and cannot tolerate stainless steel appliances or appliances with stainless steel liners.

Methods of Making Coated Appliances

The coatings 46 described in the present disclosure can be prepared on a substrate using various film deposition methods known in the art. However, unexpected and superior properties of the coatings 46 were obtained through the use of particular processing conditions, as described below.

Prior to deposition, the body 44 may undergo surface treatments, such as plasma etching and reactive ion etching, to provide good bonding between the body 44 and the coating 46. Surface treatments may also include cleaning steps, such as solvent washing, mechanical wiping and polishing, and combinations thereof.

Optionally, one or more adhesion promoting layers, such as one or more tie layers, may also be disposed between the body 44 and the coating 46. Particularly suited tie layers include metals and metal oxides, including titanium and titanium oxide.

The coating 46 may then be deposited on the body 44 using a variety of methods. Examples of suitable deposition techniques include chemical vapor deposition, plasma-enhanced chemical vapor deposition, sputter coating, e-beam reactive coating, and combinations thereof. Metallic and ceramic mask features may be used to limit the deposition to slots 36 and 40.

One particularly suitable deposition technique for forming coatings 46 is physical vapor deposition (PVD) by sputtering. In this technique, atoms of the target are ejected by high-energy particle bombardment so that they can condense onto a substrate as a thin film. The high-energy particles used in sputter-deposition are generated by a glow discharge, or a self-sustaining plasma created by applying a radio frequency field to argon gas.

In one exemplary method, the coating 46 is formed using a yttria-stabilized zirconia insulating target in a reduced-pressure atmosphere of argon and oxygen. In some embodiments, the yttria-stabilized zirconia target has a yttrium (III) oxide composition ranging from 5 to 15 molar percent relative to pure zirconia. The deposition process continues for a sufficient duration to build up a suitable layer thickness of the yttria-stabilized zirconia on the body 44, thereby forming the coating 46. After the deposition is completed, the coating 46 can optionally undergo post-deposition treatments, such as polishing, to enhance the aesthetic qualities of the bracket 22.

Advantageously, the layer thickness of the stabilized zirconia coating can be tailored to provide the surface properties (e.g. friction and hardness) desired. For example, as the layer thickness approaches zero, the surface properties may approach that of the uncoated substrate. On the other hand, at high layer thicknesses, the surface properties may assume those of bulk stabilized zirconia. At intermediate layer thicknesses, the deposition process can be precisely timed to provide properties residing between these endpoints. The coverage of the coating 46 may be controlled by masking the bracket 22 prior to deposition such that the coating 46 is selectively applied on the outer surfaces of the archwire slot 36. It is further noted that different properties, such as abrasion resistance and dynamic coefficient of friction, may change at different rates with respect to coating thickness.

The sample stage holding the bracket 22 can be static or can be moved during the deposition process. In some embodiments, the coating thicknesses are deposited in a non-uniform fashion based on the relative positions between the stabilized zirconia target and the sample stage. In some embodiments, the coating 46 on the bottom of the archwire slot 36 may be intentionally made thicker than the coating 46 on the sidewall of the archwire slot 36. This can allow surface properties to vary depending on the nature of the contact between the archwire 24 and the bracket 22. If desired, for example, the sliding friction associated with the bottom of the archwire slot 36 can be made lower than that associated with the side walls.

One of the problems discovered with respect to conventional stabilized zirconia coatings is the apparent inverse relationship between desirable coating properties. For example, conventional coating methods have difficulties in providing a stabilized zirconia coating that simultaneously displays both a high level of robustness and a low color cast. Stabilized zirconia coatings that are deposited at low pressures (less than 20 millitorr) tend to display the highest abrasion resistance, but sometimes have an undesirable color cast. On the other hand, stabilized zirconia coatings that are deposited at higher pressures (20 millitorr or higher) generally yield coatings with improved color for dental applications, yet these coatings also tend to have relatively poor abrasion resistance.

It was discovered, however, that this technical problem can be overcome by preparing stabilized zirconia coated appliances using a two-step process. First, a virgin stabilized zirconia coating is deposited onto the appliance substrate at very low pressures as described above. Second, the stabilized zirconia coating is heat treated in an oxygenated environment. The heat treatment step preferably occurs at temperatures ranging from 300 to 900 degrees Celsius, more preferably at temperatures ranging from 450 to 800 degrees Celsius, and most preferably at temperatures ranging from 600 to 700 degrees Celsius.

In some embodiments, the oxygenated environment is air, which contains about 21 percent oxygen by volume. In some embodiments, the heat-treatment step is sustained for at least 15 minutes, at least 30 minutes, or at least 1 hour. Following heat-treatment, the coated appliance is allowed to cool in air at ambient temperatures.

Advantageously, the heat-treatment step decolorizes the stabilized zirconia coating (e.g. reduces $\Delta L^*$, $\Delta a^*$, and/or $\Delta b^*$ with respect to the coating prior to heat-treatment), while preserving its abrasion resistance. As a result, the two-step process allows coatings to be prepared that simultaneously achieve a high degree of abrasion resistance and minimal color cast. For example, this advantage may be achieved by heat-treating stabilized zirconia coatings deposited by physical vapor deposition sputtering at pressures of 20 millitorr or less, 10 millitorr or less, or even 5 millitorr or less.

As an additional benefit, the two step process provides a more robust manufacturing process. By addressing the issues of coating integrity and coating color in separate steps, the process eliminates a constraint in the deposition step thereby enlarging the processing window. For example, it is possible to optimize the conditions of the deposition step to maximize the robustness of the coating without color considerations, given that the optimized coating can be subsequently decolorized. One benefit of conducting the deposition step at lower pressures is a higher rate of deposition.

Figure 4:
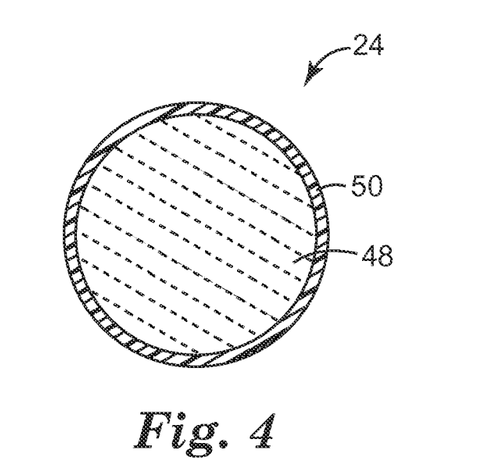
FIG. 4 is a sectional view of an archwire of the orthodontic appliance of the present invention, showing cross-sectional components of the archwire.

An alternative embodiment of the present invention is shown in FIG. 4, which shows a sectional view of archwire 24, taken in a plane perpendicular to the longitudinal length of archwire 24. As shown, archwire 24 contains substrate 48 and coating 50. Substrate 48 is a standard archwire substrate, and may compositionally include a metallic material, such as stainless steel, beta-titanium, or Nitinol (i.e., a nickel-titanium shape-memory alloy). While archwire 24 is shown in having a round cross-sectional configuration in FIG. 4, archwire 24 may alternatively exhibit other geometric cross-sections (e.g., a square or rectangular cross-section). Coating 50 is a stabilized zirconium oxide coating deposited substantially around the entire surface of substrate 48. Examples of suitable materials and layer thicknesses for coating 50 are the same as those discussed above for coating 46 (shown in FIG. 3). The materials may also be deposited in the same manner as discussed above to provide a thin layer substantially surrounding substrate 48.

In this embodiment, the archwire 24 contains a stabilized zirconia coating 50 for enhancing abrasion resistance while reducing galling and frictional resistance between the bracket 22 and the archwire 24. Optionally, the bracket 22 is a standard uncoated orthodontic bracket. The thin layer of coating 50 allows the use of the archwire 24 with standard orthodontic brackets without requiring modifications to the archwire slots to retain the benefits of the coating 50. When the practitioner adjusts archwire 24 during the orthodontic treatment, the reduced galling and frictional resistance provided by coating 50 permits bracket 22 to more easily slide along the archwire slot of the archwire 24. This reduces time and effort required to complete the orthodontic treatment in the same manner as discussed above for bracket 22 in FIGS. 2 and 3.

In another alternative embodiment, bracket 22 may include coating 46, as discussed above, and archwire 24 may contain coating 50. This further reduces galling and the frictional resistance between bracket 22 and archwire 24 by having coating 46 contact coating 50 when archwire 24 engages bracket 22. Accordingly, orthodontic appliances 12 of the present invention may include a variety of orthodontic articles, such as brackets (e.g., brackets 22 and 26) and archwires (e.g., archwires 24 and 28) that contain stabilized zirconium oxide coatings. This allows the brackets to slide more easily along the archwires during orthodontic treatment, thereby increasing efficiency and decreasing treatment time.

In other embodiments, the disclosed coatings may be advantageously applied, and optionally heat-treated, on the outer surfaces of other dental articles previously enumerated, including restoratives, replacements, inlays, onlays, veneers, full and partial crowns, bridges, implants, implant abutments, copings, anterior fillings, posterior fillings, and cavity liners, and bridge frameworks. In still other embodiments, a dental restoration is performed by preparing a dental site to be restored, and then bonding the coated dental article to the dental site.

EXAMPLES

Objects and advantages of the disclosed embodiments are further illustrated by the following examples. The particular materials and amounts thereof recited in these examples, as well as other conditions and details, should not be construed to unduly limit this invention. Unless otherwise indicated, all parts and percentages are by weight and all molecular weights are weight average molecular weight.

Fabrication of the Alumina Substrate

Alumina discs, having a thickness of 1.6 millimeters, a diameter of 33 millimeters, and a nominal surface finish of $R_a$ of 0.02 to 0.03 micrometers, were obtained from SPT Roth Ltd. of Lyss, Switzerland. The grain size and translucency of these materials were in accordance with the fine-grain alumina properties disclosed in issued U.S. Pat. No. 6,648,638 (Castro, et al.).

Physical Vapor Deposition of the Coating

The fine-grain ceramic substrates were coated with yttria-stabilized zirconia using a process called physical vapor deposition (PVD) by sputtering. In this process, a glow plasma discharge, localized around a "target" by a magnet, bombards the material and sputters some away as a vapor. The stabilized zirconia coatings were deposited using a custom-built sputtering apparatus (available from Innovative Systems Engineering in Warminster, Pa.) operating in radio frequency mode. The apparatus was outfitted with a load-locked sample chamber and a four-target sputtering chamber. Each target was contained within a separate 6-inch diameter indirectly-cooled cathode (available from Angstrom Sciences in Duquesne, Pa.).

The target material used in the sputtering process had a chemical composition of 8 molar percent yttria-stabilized zirconia (obtained from Kurt J. Lesker Company in Clairton, Pa.). The yttria-stabilized zirconia target had a diameter of 6 inches and a thickness of 0.125 inches, and was bonded to a copper backing plate. The stabilized zirconia coatings were deposited at an input power of 400 watts using a radio frequency (13.56 MHz) power supply. Coatings were deposited both in pure argon and also in argon with small pressures of oxygen (about 2 to 3 percent by volume). Pressures for the depositions ranged from 5 millitorr to 20 millitorr, and was controlled using a butterfly valve. Gas flow was maintained at 100 standard cubic centimeters per minute (sccm) for all depositions. Stabilized zirconia coatings were deposited onto the ceramic substrate over a period of time sufficient to provide a coating having a layer thickness of approximately 500 nanometers.

Gloss Measurements

Gloss, as used herein, is the ability of a surface to reflect visible light in specular directions. The higher the gloss, typically the smoother the material. Gloss measurements were made using a Novo-Curve Micro Gloss Meter (available from Gloss-Meters USA in New York, N.Y.) at an incident angle of 60 degrees according to ASTM standards D523/D2457.

Dynamic Coefficient of Friction Measurements

The dynamic coefficient of friction was measured based on the interaction of two specimens. The first was a flat specimen and the second was a spherically ended specimen (ball specimen), which slides against the flat specimen. A downward vertical load was applied by the ball specimen against the flat specimen, which was horizontally mounted. To measure frictional forces, the flat specimen was then translated in a linear, back and forth sliding motion relative to the ball specimen. The ball is mounted to a stiff lever acting as a force transducer in the horizontal axis. As the flat specimen is translated relative to the ball specimen, the resulting frictional forces acting between the two specimens are measured by the very small deflections of the lever using a linear variable differential transformer (LVDT) sensor.

This test was generally conducted in accordance with the ASTM G133 Standard Test Method for Linearly Reciprocating Ball-on-Flat Sliding Wear. However, the following deviations were noted:

1) The ball radius was 3 millimeters instead of 4.76 millimeters.
2) The normal force is 2 newtons instead of 25 newtons.
3) The stroke length is 4 millimeters instead of 10 millimeters.
4) The oscillating frequency is 0.01 hertz instead of 5 hertz.
5) The test duration is 8 minutes instead of 16 minutes and 40 seconds (sliding distance is 0.04 meters).

The above deviations were made to simulate the typical forces and conditions an orthodontic archwire would exert against the bracket during the course of orthodontic treatment. Five cycles were run per test, with a maximum linear speed of 0.0001 meters per second, and a frequency of oscillation of 0.01 cycles per second. The static partner (ball specimen) was made from SS440 grade 25 stainless steel. Between tests, acetone was used to clean the static partner, while the isopropyl alcohol was used to clean the sample (flat specimen). All tests were conducted in air with a relative humidity ranging from 47 to 49 percent at temperatures ranging from 23.7 to 25 degrees Celsius. No lubricant was used.

Testing was performed at EP Laboratories (located in Irvine, Calif.) with a Pin-on-Disk Tribometer (Serial No. 18-281) with a linear module (Serial No. 1-120), and InstrumX software, version 2.7, (all available from CSM Instruments Inc., in Needham, Mass.).

Abrasion Testing

An abrasion test apparatus was used to qualitatively examine the abrasion resistance of the coatings. The abrasion apparatus used a 1"×1" section of a green, #220 Heavy Duty SCOTCH-BRITE brand scour pad attached to the head of a Henry Schein #900-4082 ACCLEAN brand toothbrush using 3M DP 100 epoxy. This was then mounted to a motorized actuator. The coated sample disc to be tested was then submerged in a water-filled trough that was positioned underneath the toothbrush head that was oscillated at a stroke rate of 30 cycles/minute. One stroke cycle is equal to two passes of the scour pad over the sample. The actuator assembly was lowered such that the scour pad exerted a normal force of 400 grams against the sample. The force varied slightly due to fluctuations in mass of the toothbrush head assembly. This force has been determined to be similar to those forces typically encountered in toothbrushing. After 4000 cycles, the test was stopped and the sample disc removed for observations relating to abrasion resistance.

The testing was continued until a total of 16000 cycles was achieved. The section of SCOTCH-BRITE brand scour pad was replaced with a new section after every 4000 cycles of testing.

Color Testing

The sample ceramic brackets of Examples 1 and 2 and Comparative Example A were each quantitatively measured for color pursuant to the following procedure. The color measurements were performed to record the color of the sample ceramic bracket as it appeared on a white standard background. The background was commercially sold under the trade designation "SRS-99-010" white reflectance standard background, from Labsphere, Inc., North Sutton, N.H. The color measurements were performed using a Hunter Ultrascan XE integrating sphere spectrophotometer (available from Jasco, Inc. in Easton, Md.).

To test the color, a sample ceramic bracket was placed on the reflectance standard background (white or black), within a 4-millimeter diameter test aperture. This procedure measured the appearance of the bracket as well as a small portion of the reflectance standard background. A Light Source D65 (6504 Kelvin light) with an observer angle of ten degrees was used (this setting is typically represented as D65/10°). The data was recorded for specular reflection excluded (SPEX) to minimize gloss effects.

The color measurement system relied on the Commission Internationale de l'Eclairage L*a*b* scoring system. The system measured L lightness (L*), red/green (a*), and yellow/blue (b*) for each sample ceramic bracket. The overall difference between samples is expressed as a ΔE value:

$$\Delta E^*_{ab} = \sqrt{[(\Delta L^*)^2 + (\Delta a^*)^2 + (\Delta b^*)^2]}$$

,where ΔL*, Δa*, and Δb* are the differences of the L*, a*, or b* readings of the sample ceramic bracket of Example 2 and the corresponding readings of a test standard.

Here, the test standard was the sample ceramic bracket of Comparative Example A, and the readings used for the test standard were the average readings from three separate sample ceramic brackets of Comparative Example A. Table 1 provides the L*, a*, b* readings and the ΔE values for the sample ceramic brackets of Examples 1 and 2 and Comparative Example A, with the use of a white reflectance standard background.

Chemical Durability Testing

Discs were tested for chemical durability using the procedure described in ISO 6872-2008. These tests deviated from the ISO 6872-2008 procedure in that the discs tested had a surface area that was slightly smaller than that specified in the procedure. Based on the mass loss of the coating relative to that of the uncoated alumina substrate, the coatings can be assessed for their resistance to chemical erosion.

Examples 1-5 and Comparatives A-D

Examples 1-5 were prepared by fabricating alumina discs as described above and then coating the discs with stabilized zirconia under the conditions shown in Table 1. Deposition times generally ranged from about 40 minutes to about 120 minutes, depending on the gas composition. The presence of oxygen was observed to significantly decrease deposition rate, resulting in longer deposition times. Deposition pressure was also observed to influence deposition rate, but to a lesser extent. Overall sputtering rates for pure argon at 400 watts were approximately 12 nanometers per minute.

In all cases, the load lock was evacuated to a pressure of $4.5 \times 10^{-5}$ torr prior to moving the sample into the deposition chamber. Each deposition run used a slow power ramp-up to 400 watts and a 5 minute stabilization period at 400 watts with the sample shutter closed prior to the actual coating deposition. The samples were observed to increase in temperature to approximately 60 to 70 degrees Celsius as a result of the deposition.

Comparatives A and C were 316L stainless steel strips and Comparatives B and D were uncoated alumina discs. Friction testing was conducted on Examples 1-5 and Comparatives A-D. The results are shown in Table 1.

TABLE 1

Friction Coefficients for Examples 1-5 and Comparatives A-D

| Example/ Comparative | Substrate | Coating | Pressure (millitorr) | Friction coefficient (mu) |
|---|---|---|---|---|
| 1 | Alumina | Stabilized zirconia | 5 | 0.11 ± 0.0056 |
| 2 | Alumina | Stabilized zirconia | 10 | 0.18 ± 0.014 |
| 3 | Alumina | Stabilized zirconia | 10 | 0.14 ± 0.023 |
| 4 | Alumina | Stabilized zirconia | 5 | 0.12 ± 0.052 |
| 5 | Alumina | Stabilized zirconia | 20 | 0.15 ± 0.016 |
| A | Alumina | None | n/a | 0.35 ± 0.065 |
| B | 316L SS | None | n/a | 0.11 ± 0.022 |
| C | Alumina | None | n/a | 0.46 ± 0.047 |
| D | 316L SS | None | n/a | 0.11 ± 0.0045 |

Examples 6-11

Examples 6-11 were prepared using methods similar to those used to prepare Examples 1-5. Qualitative abrasion testing was performed using the Abrasion Test procedure described earlier. As shown, coatings were deposited at sputter pressures ranging from 5 to 20 millitorr. The conditions used to make these Examples and the respective test results are provided in Table 2 below.

In Example 7, a titanium tie layer was introduced as an additional layer interposed between the alumina substrate and the stabilized zirconia coating. The titanium tie layer was coated using the same d.c. magnetron sputtering system as that used for the stabilized zirconia deposition. Deposition of the tie layer was conducted at a pressure of 10 millitorr, a gas flow rate of 70 sccm argon, and an input power of 400 watts. A deposition time of 6 seconds was used, yielding a tie layer thickness of approximately 2 nanometers.

TABLE 2

Abrasion Test Results for Examples 6-11

| Example | Oxygen level (percent by volume) | Pressure (millitorr) | Tie layer | Heat-treatment | Abrasion resistance |
|---|---|---|---|---|---|
| 6 | 2-3% | 20 | None | None | Significant chipping |
| 7 | 2-3% | 10 | Titanium | None | Significant chipping |
| 8 | 2-3% | 10 | None | None | Significant chipping |
| 9 | 2-3% | 5 | None | None | No chipping, minimal wear |
| 10 | 0% | 5 | None | None | No chipping, minimal wear |
| 11 | 0% | 5 | None | 650° C. for 30 minutes | No chipping, minimal wear |

Examples 12-16 and Comparative Example E

Additional specimens were prepared for gloss, color, and chemical durability testing. These specimens were again prepared using methods similar to those used in preparing Examples 1-5. The conditions used to make these specimens are listed in Table 3. The measured gloss, color, and chemical durability (i.e. mass loss) of these specimens are provided in Table 4.

TABLE 3

Coating Parameters for Examples 12-16 and Comparative E

| Example/Comparative | Substrate | Coating | Oxygen level | Pressure (millitorr) | Heat-treatment |
|---|---|---|---|---|---|
| 12 | Alumina | Stabilized zirconia | 2-3 | 5 | None |
| 13 | Alumina | Stabilized zirconia | 2-3 | 10 | None |
| 14 | Alumina | Stabilized zirconia | 2-3 | 20 | None |
| 15 | Alumina | Stabilized zirconia | 0 | 5 | None |
| 16 | Alumina | Stabilized zirconia | 0 | 5 | 650° C. for 30 minutes |
| E | Alumina | None | n/a | n/a | None |

TABLE 4

Color, Gloss, and Chemical Durability of Examples 12-16 and Comparative E

| Example/Comparative | l* | a* | b* | ΔE | 60° Gloss | Mass loss |
|---|---|---|---|---|---|---|
| 12 | | | | | 159 | |
| 13 | | | | | 155 | |
| 14 | | | | | 140 | |
| 15 | 72.7 | 0.29 | 3.84 | 4.2 | 156 | |
| 16 | 75.7 | −0.17 | 0.89 | 3.9 | 155 | 10.3 |
| E | 72 | −0.58 | −0.25 | 0.0 | 100 | 10.3 |

Only Example 16 and Comparative E were tested for chemical durability. Based on the mass loss measurements shown in Table 4, the stabilized zirconia coating met the minimum requirements for solubility as set out by ISO 6872-2008.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

What is claimed is:

1. A method of making a coated dental article, the method comprising:
   providing a dental article having an outer surface; and
   depositing on at least a portion of the outer surface a coating comprising zirconia that is at least partially stabilized by an alloying compound selected from the group consisting of yttrium oxide, calcium oxide, cerium oxide, magnesium oxide and combinations thereof, wherein depositing the coating takes place at a pressure of 10 millitorr or less; and
   heat-treating the coating in an oxygenated environment at a temperature ranging from 300 to 700 degrees Celsius, wherein the coating has a layer thickness ranging from 400 to 700 nanometers
   wherein the coating after heat-treating exhibits enhanced abrasion resistance as evidenced by a lack of chipping after 16000 cycles of the Abrasion Resistance Test; and
   wherein the dental article is an orthodontic bracket having an archwire slot, and wherein the coating is deposited on a least a portion of the archwire slot.

2. The method of claim 1, wherein the coating is heat-treated at a temperature ranging from 600 to 700 degrees Celsius.

3. The method of claim 1, wherein the heat-treated coating displays a Δa* value greater than 0.5 relative to an uncoated article for a white reflectance standard background before heat-treatment and a Δa* value of 0.5 or less relative to an uncoated article for a white reflectance standard background after heat-treatment.

4. The method of claim 1, wherein the heat-treated coating displays a Δb* value greater than 1.5 relative to an uncoated article for a white reflectance standard background before heat-treatment and a Δb* value of 1.5 or less relative to the uncoated article for a white reflectance standard background after heat-treatment.

5. The method of claim 1, wherein depositing the coating takes place at a pressure of 5 millitorr or less.

6. The method of claim 1, wherein depositing the coating comprises physical vapor deposition of the coating, and wherein the physical vapor deposition is conducted using a stabilized zirconia target.

7. The method of claim 6, wherein the stabilized zirconia target comprises yttrium (III) oxide.

8. The method of claim 7, wherein the stabilized zirconia target has a yttrium (III) oxide composition ranging from 5 to 15 molar percent.

9. The method of claim 1, wherein the coating has a 60 degree gloss value exceeding 150 percent that of the uncoated article.

10. The method of claim 1, and further comprising masking the bracket such that the coating is selectively applied on the outer surfaces of the archwire slot.

11. A coated dental article comprising:
   dental article having an outer surface; and a coating extending across at least a portion of the outer surface, the coating comprising a zirconia alloy, the zirconia alloy comprising an alloying compound selected from the group consisting of yttrium oxide, calcium oxide, cerium oxide, magnesium oxide, and combinations thereof, wherein the coating displays a $\Delta a^*$ value greater than 0.5 relative to an uncoated article for a white reflectance standard background before heat-treatment and a $\Delta a^*$ value of 0.5 or less relative to an uncoated article for a white reflectance standard background after heat treatment and a 60 degree gloss value exceeding 150 percent that of the uncoated article, and wherein the coating exhibits enhanced abrasion resistance as evidenced by a lack of chipping after 16000 cycles of the Abrasion Resistance Test wherein the dental article is an orthodontic bracket having an archwire slot, and wherein the coating is deposited on a least a portion of the archwire slot.

12. The coated dental article of claim 11, wherein the zirconia alloy has an alloying compound composition ranging from 5 to 15 molar percent.

13. The coated dental article of claim 11, wherein the dental article is an orthodontic bracket having an archwire slot including sidewalls and a bottom wall, and wherein the coating has a thickness on a portion of a sidewall that is greater than a thickness of the coating on the bottom wall, and wherein the coating has a layer thickness ranging from 400 to 700 nanometers.

14. A method of making a coated dental article, the method comprising:

providing a dental article having an outer surface; and depositing on at least a portion of the outer surface a coating comprising zirconia that is at least partially stabilized by an alloying compound selected from the group consisting of yttrium oxide, calcium oxide, cerium oxide, magnesium oxide and combinations thereof, wherein depositing the coating takes place at a pressure of 10 millitorr or less, wherein the deposited coating has a layer thickness ranging from 25 to 1000 nanometers; and subsequent to the depositing step, heat-treating the coating in an oxygenated environment at a temperature ranging from 300 to 700 degrees Celsius, such that the coating displays $\Delta a^*$ value greater than 0.5 relative to an uncoated article for a white reflectance standard background before heat-treatment and the heat-treated coating displays a $\Delta a^*$ value of 0.5 or less relative to an uncoated article for a white reflectance standard background, and wherein the heat-treated coating is translucent.

15. The method of claim 14, wherein the coating after heat-treating exhibits enhanced abrasion resistance as evidenced by a lack of chipping after 16000 cycles of the Abrasion Resistance Test; and wherein the dental article is an orthodontic bracket having an archwire slot, and wherein the coating is deposited on a least a portion of the archwire slot.

16. The method of claim 14, wherein depositing the coating takes place at a pressure of 5 millitorr or less, and wherein depositing the coating comprises physical vapor deposition of the coating.

17. The method of claim 14, wherein the heat-treated coating displays a $\Delta b^*$ value greater than 1.5 relative to an uncoated article for a white reflectance standard background before heat-treatment and a $\Delta b^*$ value of 1.5 or less relative to the uncoated article for a white reflectance standard background after heat-treatment.

18. The method of claim 14, wherein the deposited coating has a layer thickness ranging from 400 to 700 nanometers.

19. The method of claim 14, wherein the coating is heat-treated at a temperature ranging from 600 to 700 degrees Celsius.

20. The method of claim 14, wherein the dental article is an orthodontic appliance.

* * * * *

UNITED STATES PATENT AND TRADEMARK OFFICE
CERTIFICATE OF CORRECTION

PATENT NO.        : 9,539,182 B2                          Page 1 of 1
APPLICATION NO.   : 13/812006
DATED             : January 10, 2017
INVENTOR(S)       : Geoffrey Morris It is certified that error appears in the above-identified patent and that said Letters Patent is hereby corrected as shown below:

In the Claims

Column 14
Line 33, In Claim 1, delete "on a least" and insert -- on at least --, therefor.

Column 15
Line 20, In Claim 11, delete "on a least" and insert -- on at least --, therefor.

Column 16
Line 18 (Approx.), In Claim 15, delete "on a least" and insert -- on at least --, therefor.

Signed and Sealed this
Thirtieth Day of May, 2017

Michelle K. Lee
*Director of the United States Patent and Trademark Office*